United States Patent [19]
Evers

[11] Patent Number: 5,075,081
[45] Date of Patent: Dec. 24, 1991

[54] COLORIMETRIC TESTING AND MEASURING DEVICE FOR HYDRIDE GAS

[75] Inventor: Wolfgang Evers, Lübeck, Fed. Rep. of Germany

[73] Assignee: Drägerwerk Aktiengesellschaft, Lübeck, Fed. Rep. of Germany

[21] Appl. No.: 584,140

[22] Filed: Sep. 19, 1990

[30] Foreign Application Priority Data
Sep. 22, 1989 [DE] Fed. Rep. of Germany ....... 3931563
Jun. 29, 1990 [DE] Fed. Rep. of Germany ....... 4020753

[51] Int. Cl.$^5$ .......................................... G01N 30/00
[52] U.S. Cl. ...................................... 422/88; 422/86; 422/87; 436/167; 436/169
[58] Field of Search ....................... 422/86, 87, 88, 58, 422/69; 436/104, 109, 167, 169

[56] References Cited

U.S. PATENT DOCUMENTS
4,420,567 12/1983 McMahon et al. ............... 56/422

FOREIGN PATENT DOCUMENTS
0206815 12/1986 European Pat. Off. .
2022062 1/1987 Japan ............................ 422/87

Primary Examiner—Robert J. Warden
Assistant Examiner—Laura E. Collins
Attorney, Agent, or Firm—Walter Ottesen

[57] ABSTRACT

The invention is directed to a testing and measuring device for colorimetrically detecting hydride gases on a carrier which is impregnated with a solution of glycol and with a salt as an indicator. This measuring device is improved in that its long-term stability is increased and the detection of especially the smallest quantities is made possible by a clearly recognizable color change. For this purpose, only a salt, palladium chloride or palladium tetramine chloride, is present in the solution in addition to the glycol.

4 Claims, 1 Drawing Sheet

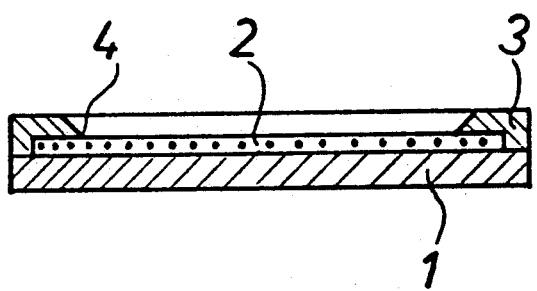

COLORIMETRIC TESTING AND MEASURING DEVICE FOR HYDRIDE GAS

FIELD OF THE INVENTION

The invention relates to a testing and measuring device for colorimetrically detecting hydride gases on a carrier which is impregnated with a solution of glycol and a salt as an indicator.

BACKGROUND OF THE INVENTION

A testing and measuring device of the kind referred to above is described in U.S. Pat. No. 4,420,567.

The reliable detection of hydride gases such as arsine or phosphine as highly toxic constituents in chemical processes, such as in the semiconductor industry, is becoming ever more necessary and requires an apparatus which can be manipulated in a simple manner and which provides a reliable indication. The known indicator operates on the principle of coloration change of an indicator substance in the presence of the hydride gas to be detected. An indicator is impregnated, for example, on a paper tape and provided with impregnation additives. The degree of coloration is measured either by a color comparison or by a linear coloration of the indicator tape. Spectro-photometric evaluation possibilities are also available.

The constituents of the known indicator include silver nitrate together with an acid and a glycol impregnated on a carrier substrate. Since the silver nitrate alone is light sensitive and a long-term stability of the indicator is assured only in short time spans, an acid additive is required to improve the long-term stability. However, this indicator provided with an acid additive also shows an unchanged detection characteristic only over a time span of approximately six months. This stabilization duration is too short to prevent a light-induced coloration of the indicator over a longer time span. However, this is desirable since the storage capability of the unused indicator is required over a significantly longer time span. Faulty measurements because of the effect of light during the detection of the hydride gas have to be avoided.

A further indicator for hydride gases is described in European Patent Publication EP-A1 206 815. A copper salt is used as a detecting reagent and especially copper carbonate is utilized. This detection system is however not sufficiently recognizable with respect to hydride gases in its coloration because the initial blue color of the indicator in the presence of the hydride gas turns black; however, this color change cannot be detected with the naked eye especially for small concentrations to be detected. Accordingly, this known indicator is only suitable where high concentrations are to be detected.

SUMMARY OF THE INVENTION

It is an object of the invention to provide an indicator of the kind described above which is so improved that its long-term stability is improved even under the action of light. It is another object of the invention that the coloration of the indicator is clearly recognizable in the presence of hydride gases and especially for the smallest quantities to be detected.

According to a feature of the invention, only palladium (II) chloride is provided as a salt in addition to the glycol.

The advantage of the invention is seen in that the indicator retains its original yellow/orange basic color even under intensive light radiation without a further additive such as an acid so that its long term stability for a period of time greater than two years is assured. A turnover of the yellow/orange coloration into a grey coloration in the presence of hydride gases is easily determined by the observer. Also, storage under increased temperatures does not lead to undesired color changes. In this way, a simple indicator solution comprising few components is obtained for detecting hydride gases. The indicator solution is stable for a long period of time and can be used for example, in indicator tapes or colorimetric indicator tubes with impregnations which are easily recognizable with respect to their color change.

The object of the invention can also be realized in that in addition to glycol, only the salt palladium tetramine chloride is present in solution. Such a device affords not only the advantage of the indicators provided with palladium (II) chloride; but instead is usable especially for detecting the smallest quantity of hydride gases in the order of magnitude of 0.01 ppm. An indicator paper impregnated with this solution remains colorless even with intensive sunlight radiation. The contrast intense color changeover from white to grey in the presence of hydride gases makes even the smallest quantity to be detected clearly recognizable.

To further increase the sensitivity, it is advantageous to use tetraethylene glycol as a glycol substance.

To produce an impregnating solution suitable for the invention, the following:

0.5 grams palladium (II) chloride and 10 mL tetraethylene glycol are filled with methanol up to 100 mL. With the solution obtained in this manner, an indicator paper with or without silica gel is impregnated as the carrier substrate and is subjected to the hydride gas as a badge. The depth of coloration of yellow/orange into grey is a measure for the presence of the pollutant quantity. Likewise, a granular silica gel charge for a colorimetric testing tube can be impregnated with the solution and can be used to detect hydride gases. The length of the coloration zone of yellow/orange into grey is a measure of the concentration of the pollutant.

A further impregnating solution suitable for the invention comprises:

0.5 grams palladium (II) chloride dissolved in 5 mL ammonia for forming palladium tetramine chloride and 10 mL tetra-ethylene glycol filled with methanol up to 100 mL. An indicator impregnated with this solution has a white coloration which changes into grey in the presence of hydride gases.

With one of the solutions obtained in the manner described above, the indicator carrier such as an indicator paper or a granular silica gel charge is impregnated and subjected to the hydride gas.

BRIEF DESCRIPTION OF THE DRAWING

The single figure of the drawing shows a section view of a testing device of the invention for detecting hydride gases.

DESCRIPTION OF THE PREFERRED EMBODIMENTS OF THE INVENTION

The testing badge shown in the drawing includes a disc-shaped badge carrier 1 on which a disc-shaped impregnated indicator paper 2 is placed. The indicator paper 2 is held with a clamping edge 3 on the badge carrier 1. The ring-shaped clamping edge 3 defines a badge opening 4 through which the hydride gas to be detected has access to the indicator paper 2. The hydride gas there reacts with the detecting solution impregnated in the paper to form a color change the depth of which is a measure for the dosage collected during the period of exposure and is determined by a comparison with a color standard. The impregnation can be dissolved palladium (II) chloride or palladium tetramine chloride.

It is understood that the foregoing description is that of the preferred embodiments of the invention and that various changes and modifications may be made thereto without departing from the spirit and scope of the invention as defined in the appended claims.

What is claimed is:

1. A testing and measuring device for colorimetrically detecting hydride gases, the device comprising:
   a carrier on which said gases are detected, said carrier being impregnated only with a solution consisting of glycol and palladium (II) chloride.
2. The device of claim 1, said glycol being tetraethylene glycol.
3. A testing and measuring device for colorimetrically detecting hydride gases, the device comprising:
   a carrier on which said gases are detected, said carrier being impregnated only with a solution consisting of glycol and palladium tetramine chloride in solution.
4. The device of claim 3, said glycol being tetraethylene glycol.